(12) United States Patent
Manginell et al.

(10) Patent No.: US 7,727,314 B1
(45) Date of Patent: Jun. 1, 2010

(54) METHODS FOR IMPROVED PRECONCENTRATORS

(75) Inventors: Ronald P. Manginell, Albuquerque, NM (US); Patrick R. Lewis, Albuquerque, NM (US); Murat Okandan, Edgewood, NM (US)

(73) Assignee: Sandia Corporation, Albuquerque, NM (US)

( * ) Notice: Subject to any disclaimer, the term of this patent is extended or adjusted under 35 U.S.C. 154(b) by 320 days.

(21) Appl. No.: 11/699,904

(22) Filed: Jan. 30, 2007

Related U.S. Application Data

(60) Provisional application No. 60/763,760, filed on Jan. 31, 2006.

(51) Int. Cl.
*B01D 53/02* (2006.01)
*G01N 25/00* (2006.01)

(52) U.S. Cl. .............. 96/146; 96/154; 422/88

(58) Field of Classification Search ............... 96/108, 96/146, 154, 413; 73/23.41, 31.05, 31.06, 73/863.11; 422/88, 89
See application file for complete search history.

(56) References Cited

U.S. PATENT DOCUMENTS

| | | | |
|---|---|---|---|
| 6,171,378 B1 | 1/2001 | Manginell et al. | |
| 6,527,835 B1 | 3/2003 | Manginell et al. | |
| 6,772,513 B1 * | 8/2004 | Frye-Mason et al. | 29/840 |
| 6,914,220 B2 | 7/2005 | Tian et al. | |
| 6,930,051 B1 | 8/2005 | Manginell et al. | |
| 7,104,113 B2 | 9/2006 | Zribi et al. | |
| 7,118,712 B1 * | 10/2006 | Manginell et al. | 422/101 |
| 7,168,298 B1 * | 1/2007 | Manginell et al. | 73/54.25 |
| 7,306,649 B2 * | 12/2007 | Boyle et al. | 95/82 |
| 7,422,724 B1 * | 9/2008 | Manginell et al. | 422/88 |

OTHER PUBLICATIONS

Lewis, Patrick R., et al., "Recent Advancements in the Gas-Phase MicroChemLab", *IEEE Sensors Journal* vol. 6, No. 3, (Jun. 2006),784-795.

Manginell, R. P., ""Recent Advancements in the Gas-Phase MicroChemLab"", *Proc. of SPIE 5591, 44*, (2004).

Tian, Wei-Cheng , et al., "Microfabricated Preconcentrator-Focuser for a Microscale Gas Chromatograph", *Journal of Microelectromechanical Systems*, vol. 12, No. 3, (Jun. 2003), 264-272.

Tian, Wei-Cheng , et al., "Multiple-Stage Microfabricated Preconcentrator-Focuser for Micro Gas Chromatography System", *Journal of Microelectromechanical Systems*, vol. 14, No. 3, (Jun. 2005), 498-507.

* cited by examiner

*Primary Examiner*—Frank M Lawrence

(57) ABSTRACT

The present invention relates generally to chemical analysis (e.g. by gas chromatography), and in particular to a compact chemical preconcentrator formed on a substrate with a heatable sorptive membrane that can be used to accumulate and concentrate one or more chemical species of interest over time and then rapidly release the concentrated chemical species upon demand for chemical analysis.

27 Claims, 20 Drawing Sheets

A

B

METHODS FOR IMPROVED PRECONCENTRATORS

CROSS-REFERENCE TO RELATED APPLICATIONS

This application claims priority to and the benefit of the filing of U.S. Provisional Patent Application Ser. No. 60/763,760, entitled "Method for Improved Preconcentrators", filed on Jan. 31, 2006, and the specification and claims thereof are incorporated herein by reference.

STATEMENT REGARDING FEDERALLY SPONSORED RESEARCH OR DEVELOPMENT

The Government has rights to this invention pursuant to Contract No. DE-AC04-94AL85000 awarded by the U.S. Department of Energy.

BACKGROUND OF THE INVENTION

The present invention relates generally to chemical analysis (e.g. by gas chromatography), and in particular to a compact chemical preconcentrator formed on a substrate with a heatable sorptive zone that can be used to accumulate and concentrate one or more sorbents over time and then rapidly release the concentrated chemical species upon demand for chemical analysis.

Presently, there is a need for autonomous, portable, handheld chemical analysis systems for the rapid and sensitive detection of particular chemicals including pollutants, high explosives and chemical warfare agents. Such miniaturized chemical analysis systems, which have been termed "chemical laboratories on a chip", are currently being developed based on gas chromatography. The requirements for these chemical analysis systems are that they provide a high chemical selectivity to discriminate against potential background interferents which may be present at up to a thousand-fold or more higher concentration, that the chemical analysis be performed on a short time scale (e.g. in a minute or less) and that the chemical analysis be performed with high sensitivity (e.g. at concentrations down to the part-per-billion level). Low electrical power consumption is also needed for field use over a prolonged time period.

Current gas-phase microanalytical systems typically comprise a gas chromatography column to separate the chemical species, or analyte, in a gas mixture, and a detector to detect the separated species. Such microanalytical systems can also include a chemical preconcentrator. The chemical preconcentrator serves the important function of selectively collecting and concentrating the analyte(s) of interest out of a large gas sample volume on a sorptive material at the inlet of the microanalytical system. In particular, selective analyte preconcentration is an essential step for early-warning, trace chemical detection in real-world, high-consequence environments where a high background of potentially interfering compounds exists. The chemical preconcentrator can deliver an extremely sharp analyte plug to the downstream gas chromatograph by taking advantage of the rapid, efficient heating of the sorbed analyte with a low-heat capacity, low-loss microheater. The very narrow temporal plug improves baseline separations, and therefore the signal-to-noise ratio and detectability of the particular chemical species of interest. Further, with a rapid enough release, there is a greatly reduced need for mechanical means of sample introduction, such as valving. See R. P. Manginell et al., "Recent Advancements in the Gas-Phase MicroChemLab," *Proc. of SPIE* 5591, 44 (2004).

Several previous microfabricated chemical preconcentrators have used a heated planar membrane suspended from a substrate as the microheater, wherein the sorptive material is disposed as a layer on a surface of the membrane to sorb the analytes from a gas stream. See U.S. Pat. No. 6,171,378 to Manginell et al., or full wafer thick slats that are in intimate contact with beads having adsorbent disposed thereon and wherein the beads are adjacent to slats that act as the microheater U.S. Pat. No. 6,914,220 to Tian et al. The slats disclosed by Tian et al. are the full thickness of the substrate in order to maximize the surface area of the beads that are coated within the sorbent zone, and therefore lose substantial heat to the substrate to which the slats attach.

Referring now to FIG. 1, prior art preconcentrator having a heated planar membrane suspended from a substrate wherein the sorptive material is disposed as a layer on a surface of the membrane to sorb the analytes from a gas stream is illustrated. A disadvantage of the design allows for heat loss via conductance from the heat elements through the membrane to the substrate along the entire perimeter of the sorbent. Reducing heat capacity and reducing heat loss between the preconcentrator and the substrate would allow for faster desorption temperature ramps at lower power.

Selective sample preconcentration is an essential step for early-warning, real-world, trace analyte detection. We have previously developed a microfabricated planar preconcentrator and three dimensional preconcentrators to address these issues for a wide array of analytes. The thermal efficiency and low heat capacity of these designs make them well suited as a platform support for adsorbent materials. Once analyte is collected on the sorbent zone, integrated thin-film resistive heaters allow for rapid thermal desorption of the sample into an analytical chain for separation and detection. Rapid heating on the order of a second or less is important for it allows the sample pulse to be delivered in a very narrow temporal plug to a gas chromatographic (GC) separation channel. This improves separations, and therefore the signal-to-noise ratio (S/N) and lower-limit of detectability.

SUMMARY OF THE INVENTION

The present invention provides a millimeter-sized or smaller chemical preconcentrator which can be used with the above miniaturized chemical analysis systems to increase the sensitivity and selectivity with which chemical analysis measurements can be made and provides for reduced energy use.

It is an aspect of the present invention to provide a preconcentrator having an improved heat capacity.

It is another object of the present invention to provide a preconcentrator having reduced heat loss to adjacent substrate.

It is yet another object of the present invention to provide a preconcentrator having improved desportion temperature ramps at lower power.

It is a further object of the present invention to provide a preconcentrator having thermal isolation support structures that suspend the sorbent zone of the preconcentrator from the substrate It is a further aspect of the present invention to provide a preconcentrator having thermal isolation support structures that provide thermal isolation of the preconcentrator from the substrate.

It is an additional object of the present invention to provide thermal isolation support structures that have a thickness that is less than full subtrate thickness.

It is an additional object of the present invention to provide thermal isolation support structures that have a thickness that is between about 90% and 0.3% of the thickness of the full subtrate.

It is an additional object of the present invention to provide thermal isolation support structures that have a thickness that is between about 50% and 10% of the thickness of the full subtrate.

Additional objects and advantages of the present invention will be apparent in the following detailed description read in conjunction with the accompanying drawing figures.

BRIEF DESCRIPTION OF THE DRAWINGS

The accompanying figures which are incorporated in and form part of the specification illustrate embodiments of the present invention and together with the description describe the invention.

DETAILED DESCRIPTION OF THE INVENTION

The present invention has been described in terms of preferred embodiments, however, it will be appreciated that various modifications and improvements may be made to the described embodiments without departing from the scope of the invention.

Figure 1:
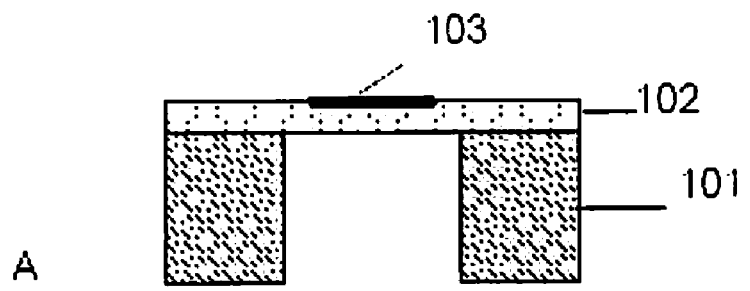
FIG. 1 illustrates prior art schematic cross section and plan views of existing membrane-isolated preconcentrators.
Figure 1:
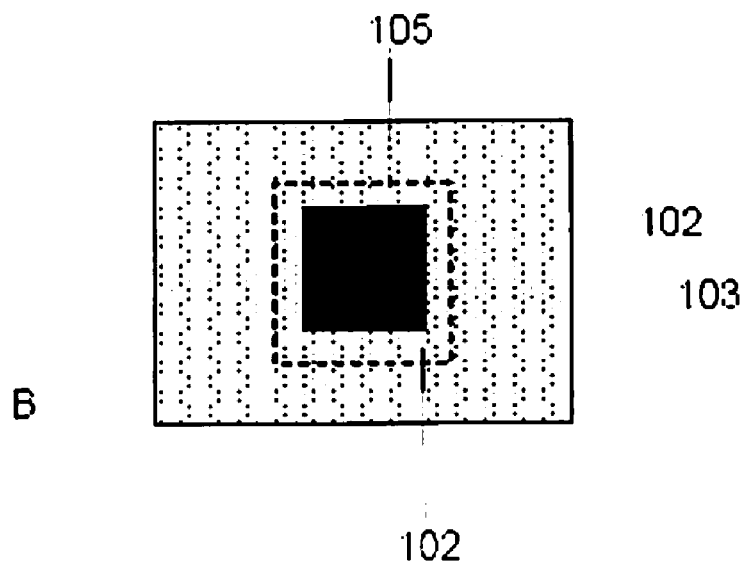
Figure 2:
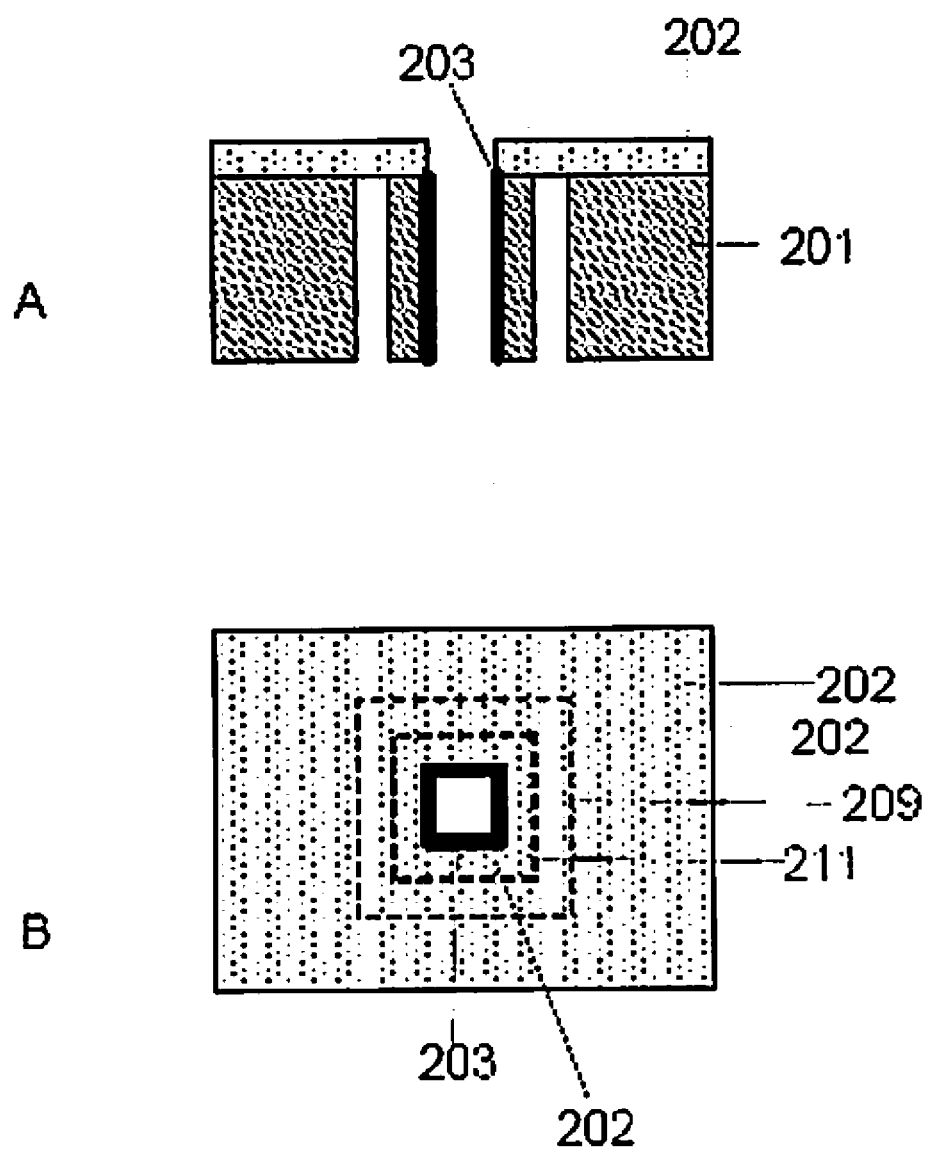
FIG. 2 illustrates a schematic cross section view (A) and plan view (B) of an existing 3-D membrane-isolated preconcentrators is illustrated.

Referring now to FIG. 1, a schematic cross section (A) and plan view (B) of an existing planar membrane-isolated preconcentrator is illustrated. Heaters are omitted for clarity and sorbent zone 103 is deposed upon the heating element. Heat is lost by thermal conduction through the membrane 102 to the substrate 101 around the entire dashed perimeter 105 which is the interface between the membrane and the substrate 101. Membranes are typically made of silicon nitride and are between about 0.5-1 um thick Referring now to FIG. 2 A-B, a schematic cross section view (A) and plan view (B) of an existing 3-D membrane-isolated preconcentrator is illustrated. Heaters are omitted for clarity and adsorbent 203 is deposed upon the heating element. Heat is lost by thermal conduction from the heating element through the membrane 202 around the entire dashed perimeter 211 and 209 to the surrounding substrate 201. Thermal conductance is proportional to the cross sectional area (e.g. width times thickness) of the conducting structure. In a preferred embodiment, when the sorbent zone is large, as in the case of the 3D preconcentrators, the thermal isolation support structures are ideally thinner than the sorbent zone to reduce heat losses. Alternatively, the sorbent zone and thermal isolation support structures can be the same thickness, provided that are not full-wafer thickness, to reduce power consumption.

Figure 3:
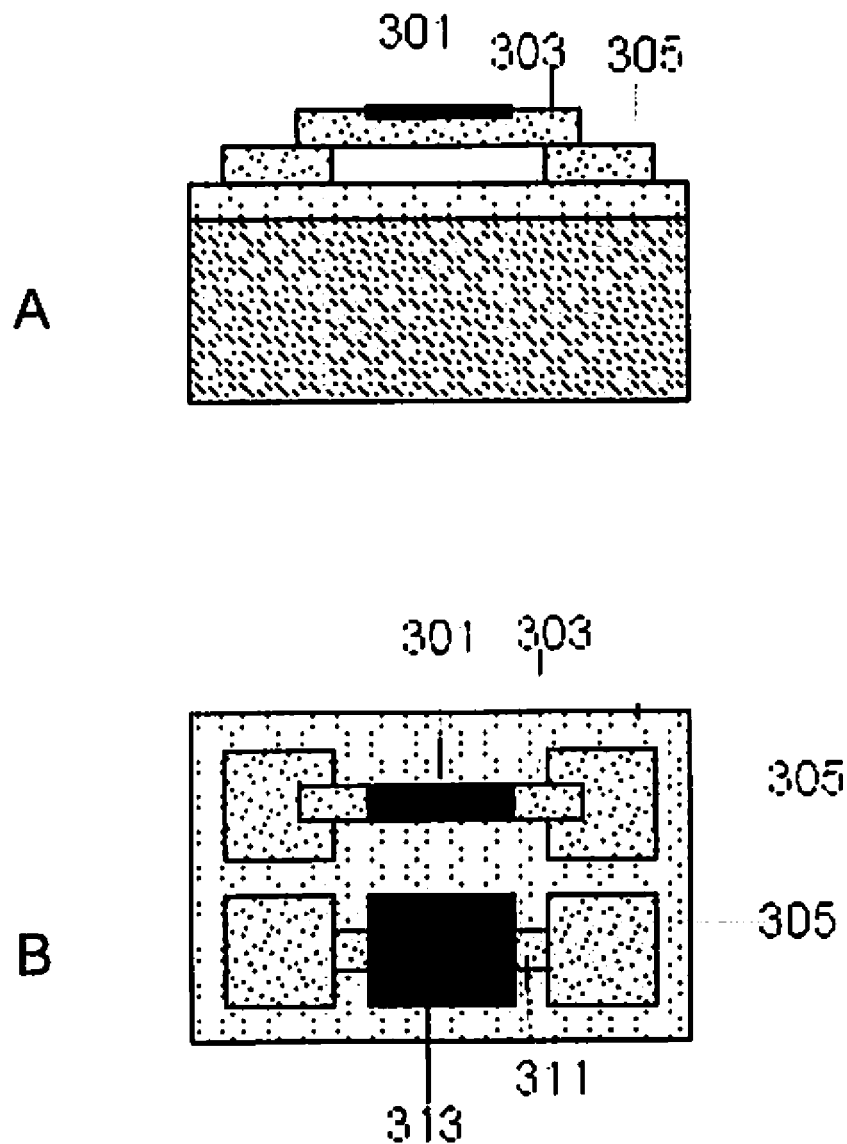
FIG. 3 illustrates a cross section view (A) and plan view (B) of preconcentrators in communication with the wafer via a thermal isolation support structure according to one embodiment of the present invention.

Referring now to FIG. 3 A-B, a cross section view (A) and plan view (B) of a preconcentrator formed on the surface of a first portion of a wafer thermally isolated with a thermal isolation support structure is illustrated according to one embodiment of the present invention. (A) illustrates a cross section view of a surface micromachined thermal isolation support structure 303 spanning an air space between the substrate 305 of a wafer and the sorbent zone 301 which is disposed upon the heating element (not shown) which itself is disposed on the substrate. (B) illustrates a planar view of a preconcentrator having a thermal isolation support structure 311 spanning an air space between the substrate 305 and the sorbent zone 313 wherein the thermal isolation support structure 311 is narrower than the sorbent zone 313 to restrict heat loss. Reduced heat capacity and heat loss allow for faster desorption temperature ramps at lower power. For analytes such as semivolatile compounds where collection is very good, smaller collection/desorption area is allowable. Therefore, the smaller adsorption zone area permitted by this system and method will permit even narrower desorption peak widths, further improving GC separations. In a preferred embodiment, an array of thermally isolated preconcentrators are employed to increase collection area. In an alternative embodiment, multiple thermal isolation support structures can provide support and isolation to a high-surface area collection zone.

The substrate used to form the chemical preconcentrator apparatus generally comprises a semiconductor (e.g. silicon or gallium arsenide), a dielectric (e.g. glass, crystalline quartz, fused silica, a plastic, a resin or a ceramic) or a combination thereof. The heating element formed on the substrate generally comprises a circuitous metal trace formed from one or more layers of deposited metals including platinum, molybdenum, titanium, chromium, palladium, gold and tungsten. The heating element could also be a semiconductor such as silicon, polysilicon, gallium arsenide for example.

Figure 4:
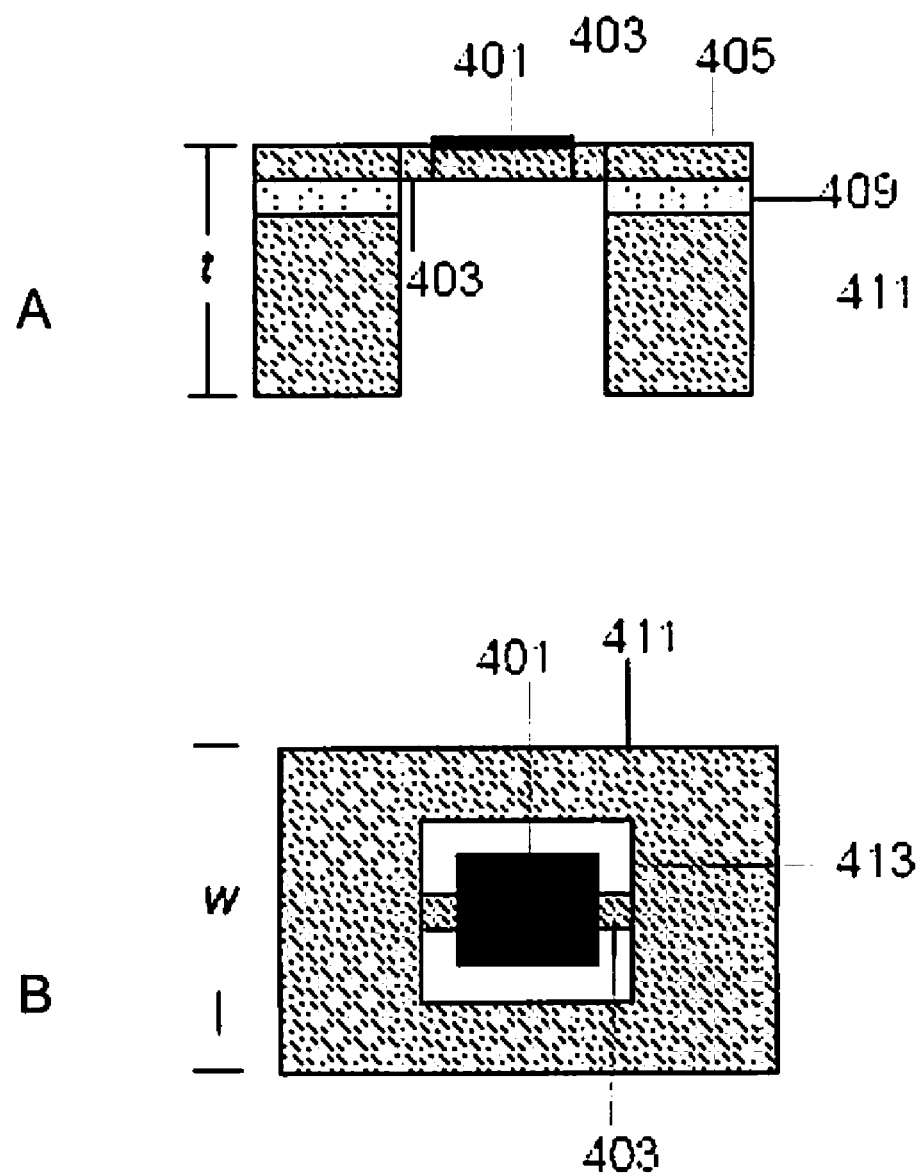
FIG. 4 illustrates a preconcentrator with thermal isolation support structures according to one embodiment of the present invention.

Referring now to FIG. 4 A-B, a cross section view (A) and plan view (B) of a preconcentrator formed on a first portion of a substrate thermally isolated from a third portion of the wafer with a thermal isolation support structure formed on a second portion of the substrate. The thickness of the first portion of the substrate is less than the thickness of the third portion of the substrate which is illustrated according to one embodiment of the present invention. The thickness of the full substrate (third portion of the substrate) is indicated by "t". Silicon-On-Insulator (SOI) fabrication with reduced-dimension thermal isolation support structures 403 relative to the sorbent zone 401 is illustrated. The SOI substrate comprises a top silicon layer 405 separated from a silicon substrate 411 by a buried oxide layer 409. A thermal isolation support structure 403 is of a thickness that is less than the thickness t of the full substrate and may span an insulating medium 413 such as air or a membrane that insulates the heating element and sorbent zone from the third portion of the substrate. The thickness of the thermal isolation support structure can be between 90% and 0.5% or between 75% and 90% of said third portion of said substrate. The width of the thermal isolation structure may be the same or different from the preconcentrator. The width of the thermal isolation support structure can range from 100% of the width of the preconcentrator to about 0.01% of the width of the preconcentrator. The first portion of the wafer may have a thickness that is the same or less than the third portion of the wafer. The heating element within a heating zone or sorbent zone is omitted for clarity.

Figure 5:
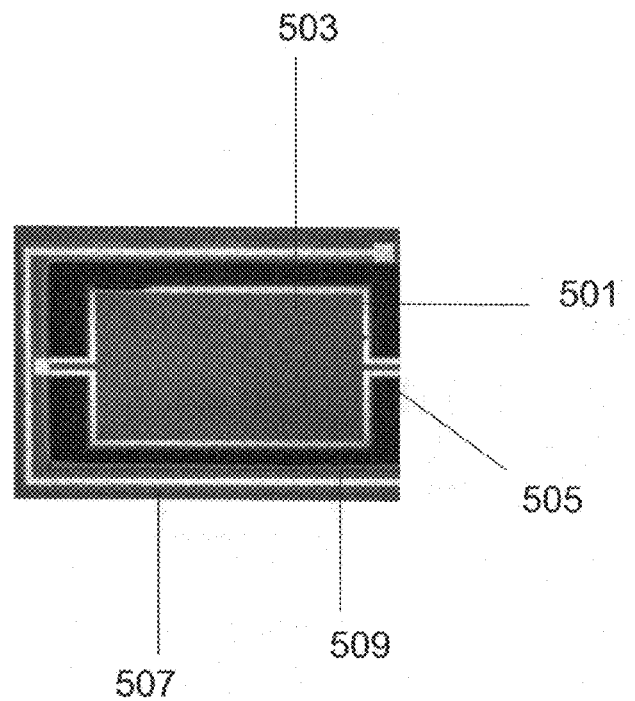
FIG. 5 is a photo of a preconcentrator as illustrated in FIG. 4.

Referring now to FIG. 5, a photo of a preconcentrator of FIG. 4 is illustrated wherein the sorbent zone 503 is disposed upon the heating element 507 and is thermally isolated from the substrate and mechanically supported via one or more thermal isolation support structures 505 which span an insulating material 509 such as a membrane or an insulating gas such as air. The dimensions of the active area of the preceoncentrator 501 is approximately 600×1500 micron while the dimensions of the thermal isolation support structure is roughly 160 micron wide by 200 micron long.

Figure 6:
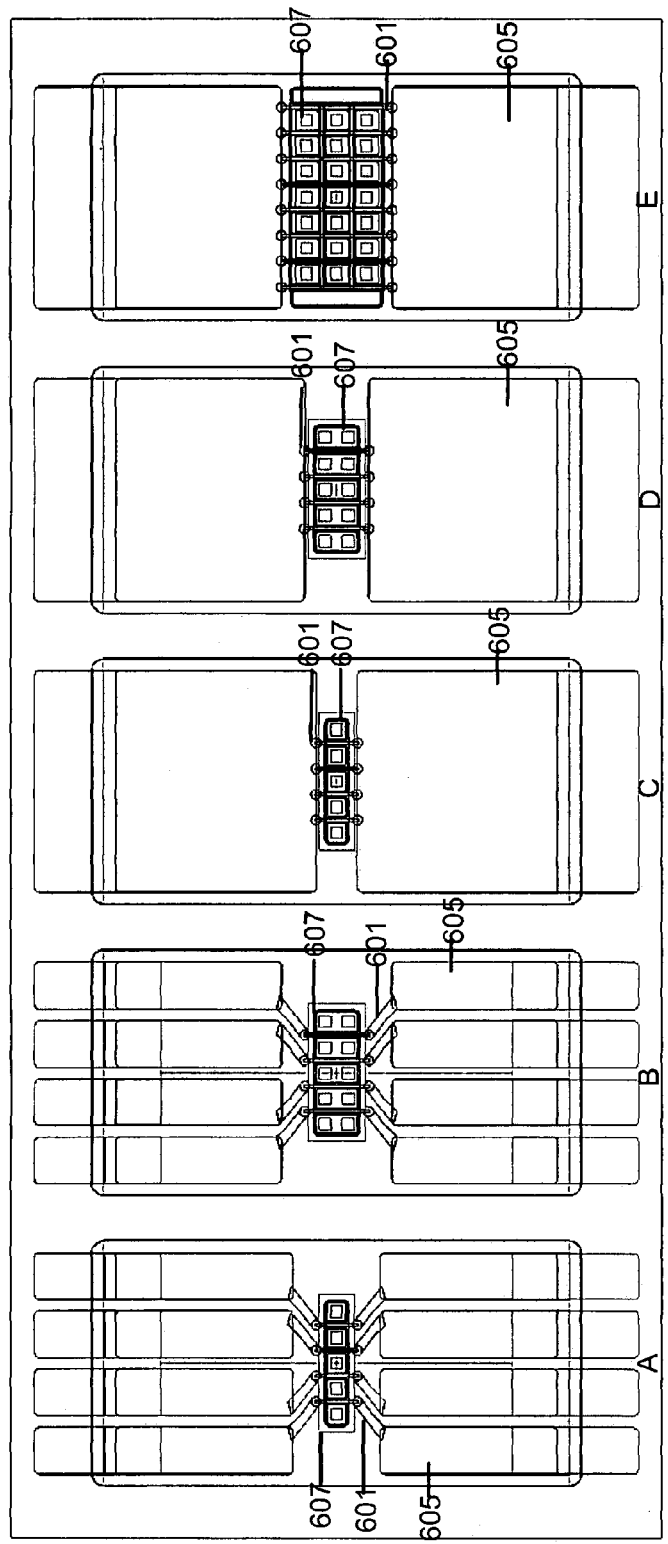
FIG. 6 illustrates multiple overlapping mask layouts for preconcentrators isolated from the subtrate with thermal isolation support structures according to one embodiment of the present invention.

Referring now to FIG. 6 A-E, multiple mask layouts for a preconcentrator isolated from the substrate with one or more thermal isolation support structures is illustrated according to one embodiment of the present invention. Each thermal isolation support structure can be made as surface micromachined support structures and/or with a through-wafer etch to allow flow through the sorbent zone and the wafer. Blocks A-B have individually-addressable thermal isolation support structures 601 supporting multiple individually addressable sorbent zones 607. The sorbent zones can be formed from a sorptive material disposed on a heating element as described previously. The sorptive material can be a microporous material which sorbs and concentrates one or more chemical species of interest from a vapor over time and which releases the chemical species when the sorptive material is heated by the resistive heating element. The sorptive material can comprise a chromatographic stationary phase material, a getter material, a sol-gel material (e.g. a sol-gel oxide which is chemically modified to enhance sorption of the chemical species of interest), or a polymer. Blocks C-D have four thermal isolation support structures 601 in parallel for added coating area of the sorbent zones 607. The thermal isolation support structures are less than the full thickness of the wafer for example between about 95% of the thickness of the wafer and less. Block E has a lattice sorbent zone 607 isolated from the substrate 605 with multiple thermal isolation support structures 601.

Figure 7:
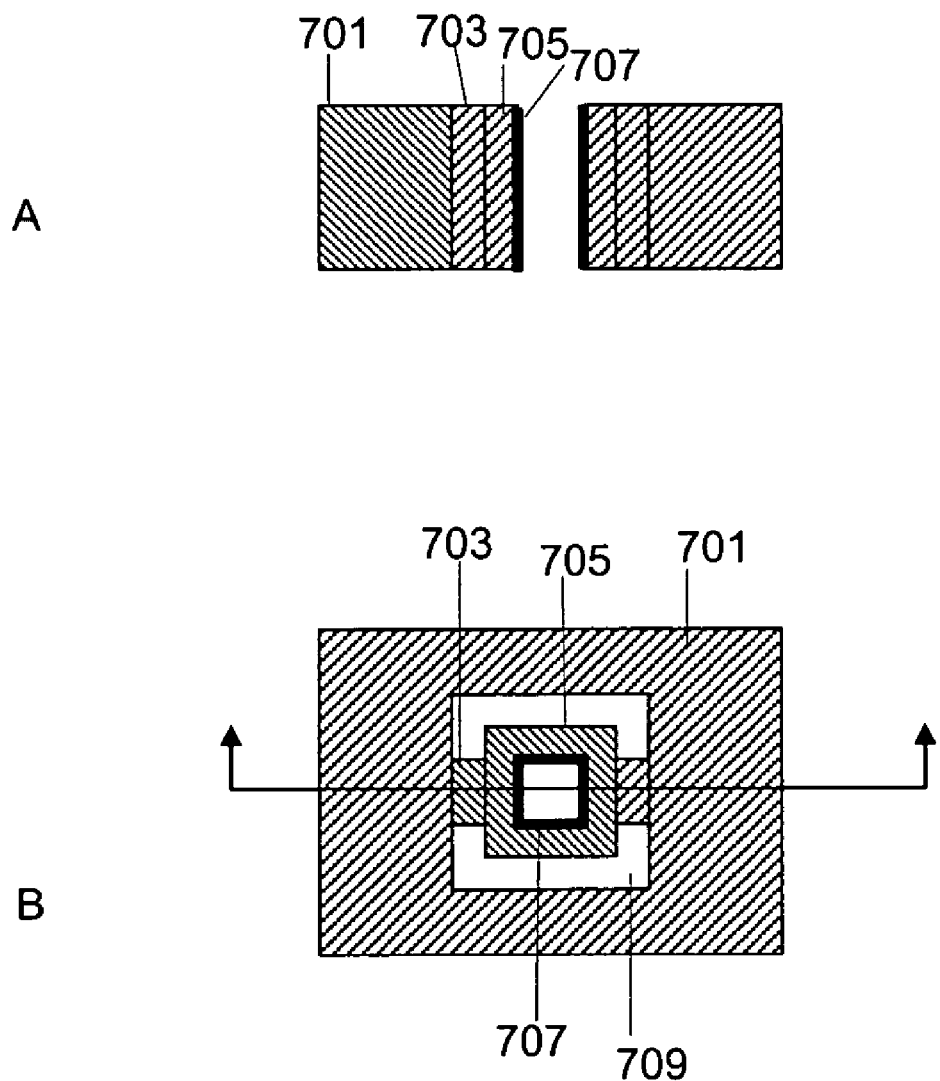
FIG. 7 illustrates a three dimensional view of a preconcentrator with full thickness slat structures as previously described in the art.

Referring now to FIGS. 7A-B, a cross section view (A) and plan view (B) of a three dimensional preconcentrator known in the art is illustrated with slat 707 structures 703 that are the same thickness as the full substrate 701. Preconcentrators with sorbent zone having full substrate thickness slats 703 span an air space 709 have been described by Tian, et al. in U.S. Pat. No. 6,914,220. Finite element modeling of preconcentrators having full substrate thickness slats shows the power losses high and not suitable for portable applications. The increase in power is in part due to the large cross-sectional area of these structures resulting from the structures having a thickness of the full substrate. As a result these structures require 5-10 watts for analyte desorption in a narrow temporal band.

Figure 8:
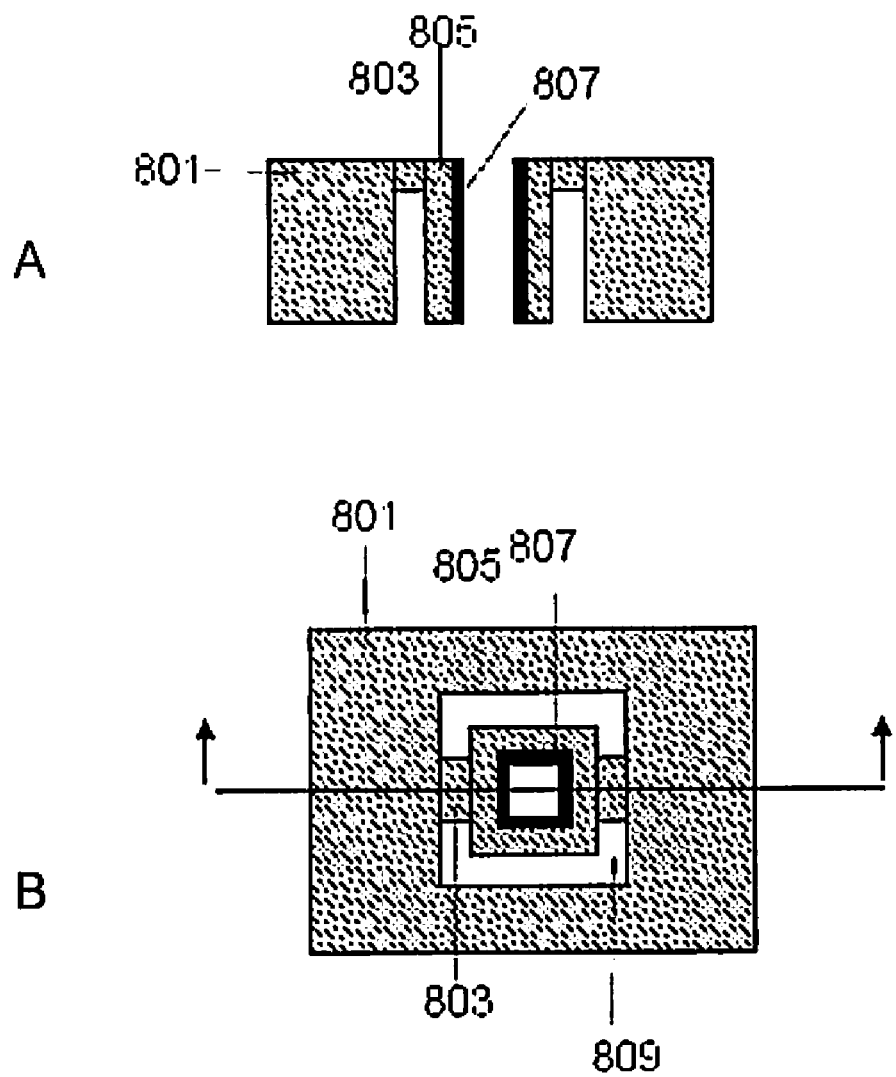
FIG. 8 illustrates a schematic three dimensional view of a preconcentrator supported by a partial thickness thermal isolation support structure to allow heating at modest power according to one embodiment of the present invention.

Referring now to FIG. 8 A-B, a cross section view (A) and plan view (B) of a schematic three dimensional according to one embodiment of the present invention preconcentrator thermally isolated and supported by a thermal isolation support structure is illustrated. A thermal isolation support structure 803 having a thickness that is less than the thickness of the full wafer 801 to allow heating of the heating element 805 to release adsorbed molecules or chemicals adsorbed onto the sorbent zone 807 at modest power. For example, these structures require 200-600 mW to raise the temperature at a rate sufficient to allow desorption of adsorbed molecules and compounds within a narrow peak suitable for analysis. Reducing the thickness of the sorbent zone 807 and the thermal isolation support structure 803 reduces power losses. In a preferred embodiment, reducing the thickness of the thermal isolation support structure 803 to be thinner than the sorbent zone 807 allows large sorbent zones to be heated at power low enough to greatly benefit field analysis, say less than 2 W.

Figure 9:
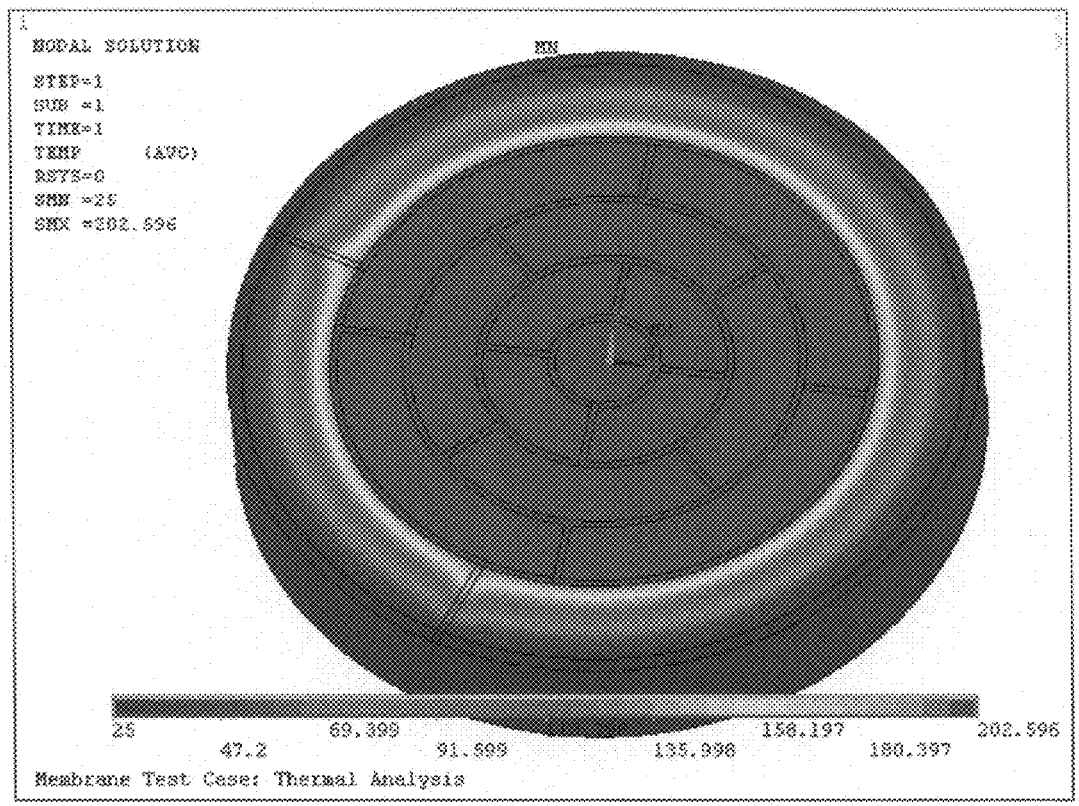
FIG. 9 illustrates ANSYS finite element prediction of the thermal behavior of 3D preconcentrator with 25 micron wide walls according to one embodiment of the present invention.

Referring now to FIG. 9, ANSYS finite element prediction of the thermal behavior of 3D preconcentrator with 25 micron wide walls is illustrated. The model was first validated against experimental steady-state and transient heating data of an actual device with 50 micron walls. In this illustration, a silicon nitride membrane provides thermal isolation of a full-thickness sorbent zone. Red indicates the area of the greatest temperature and blue indicates the area of the coolest temperature for FIGS. 9-14. 7.1 V provides 200° C.

Figure 10:
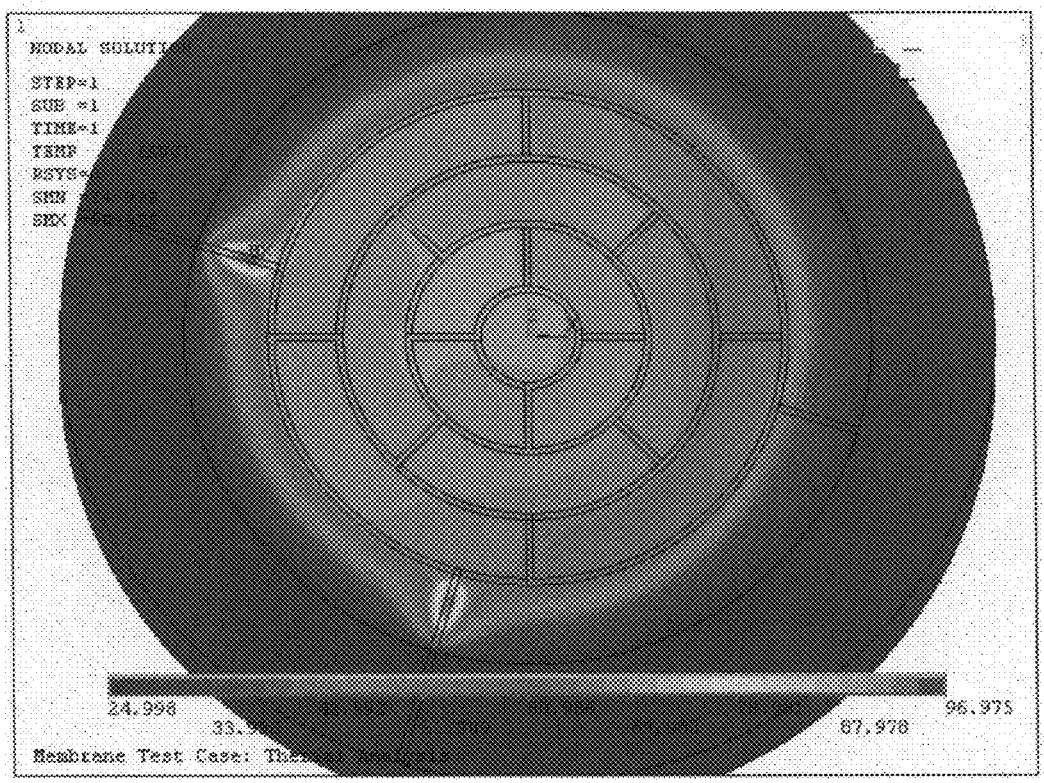
FIG. 10 illustrates ANSYS finite element prediction of the thermal behavior of 3D preconcentrator with 25 micron wide walls according to one embodiment of the present invention.

Referring now to FIG. 10, ANSYS finite element prediction of the thermal behavior of a 3D preconcentrator with 25 micron wide walls is illustrated. The model was first validated against experimental steady-state and transient heating data of an actual device with 50 micron walls. Addition of a full-thickness silicon strut spanning the air space between the substrate and a preconcentrator similar to the preconcentrator disclosed by Tian, et al. in U.S. Pat. No. 6,914,220 wherein 7.1 V only produces 92° C.

Figure 11:
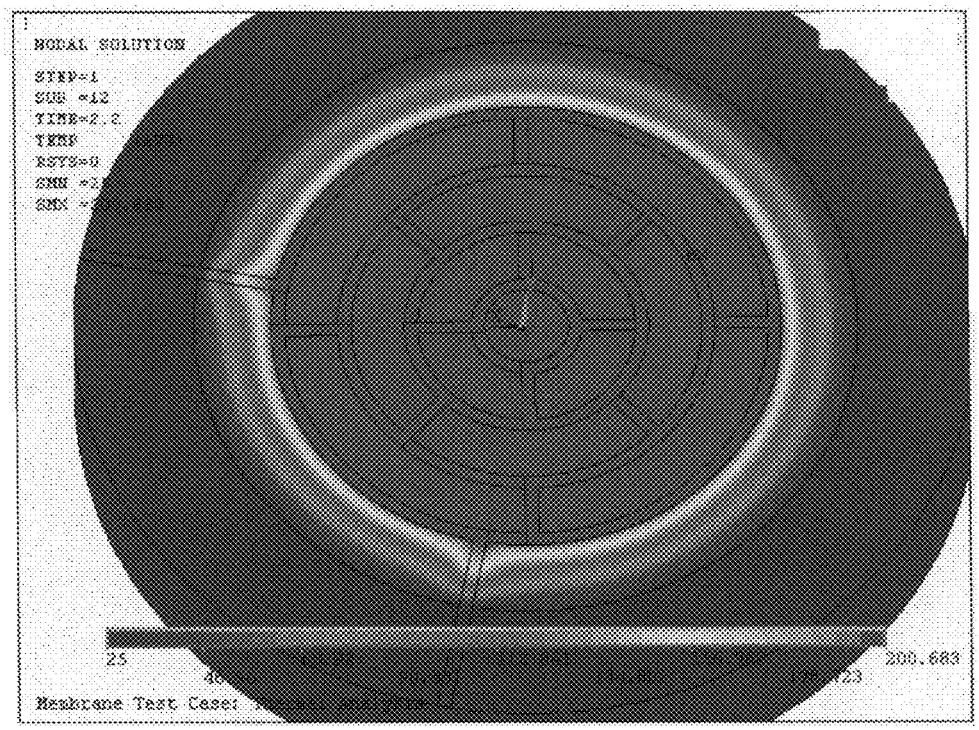
FIG. 11 illustrates ANSYS finite element prediction of the thermal behavior of 3D preconcentrator with 50 micron wide walls that are full wafer thickness according to one embodiment of the present invention.

Referring now to FIG. 11, ANSYS prediction of the thermal behavior of a 3D preconcentrator having 50 micron wide walls that are full-wafer thickness and two isolation support structures that are full wafer thickness is illustrated. 4.75 V provides 200° C.

Figure 12:
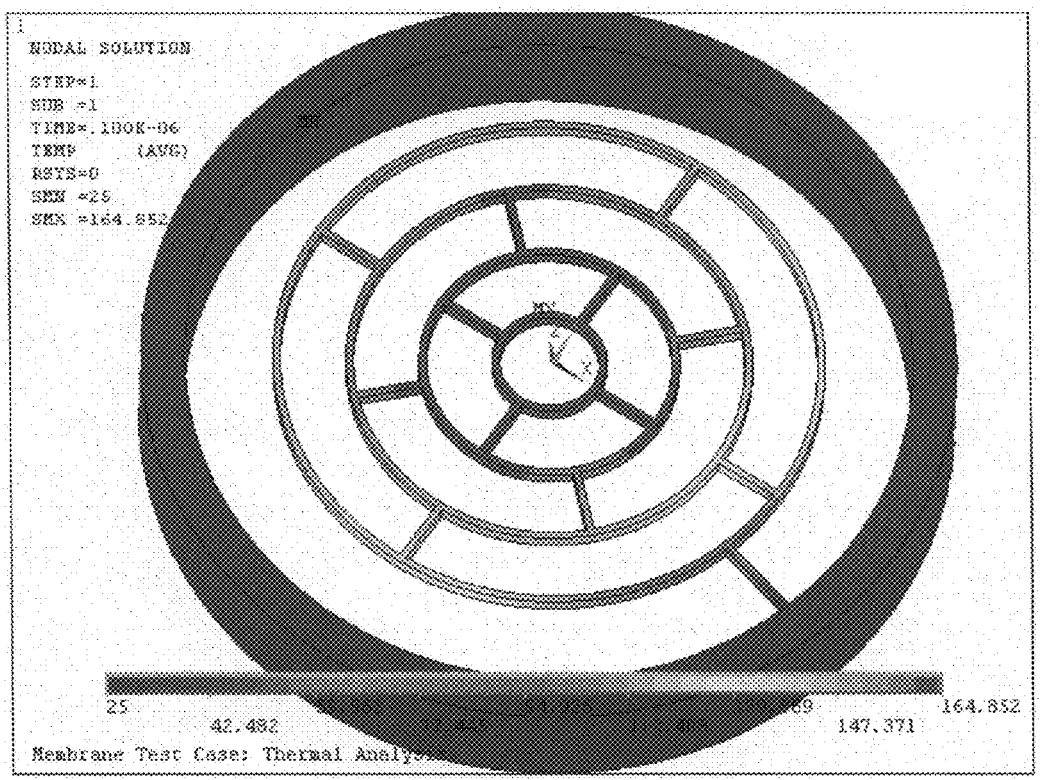
FIG. 12 illustrates ANSYS prediction of the thermal behavior of a 3D preconcentrator wherein 4.75 V provides 200° C. with 50 micron wide walls, partial thickness according to one embodiment of the present invention.

Referring now to FIG. 12, ANSYS prediction of the thermal behavior of a 3D preconcentrator is illustrated according to one embodiment of the present invention. A SiN layer, used in this design to prevent analyte from touching the surrounding cold silicon, is omitted from the view, but not the thermal model, to show the sorbent zone and thermal isolation support structure spanning the air space. Heat conduction is the flow of internal energy from a region of higher temperature to one of lower temperature by the interaction of the adjacent particles (atoms, molecules, ions, electrons, etc.) in the intervening space. Heat conductance is proportional to the area of the conducting structure (e.g. width×thickness). By reducing the width and thickness of the sorbent zone and the thermal isolation support structure to about 50 microns in thickness a temperature of 164° C. is achieved with 4.75 V.

Figure 13:
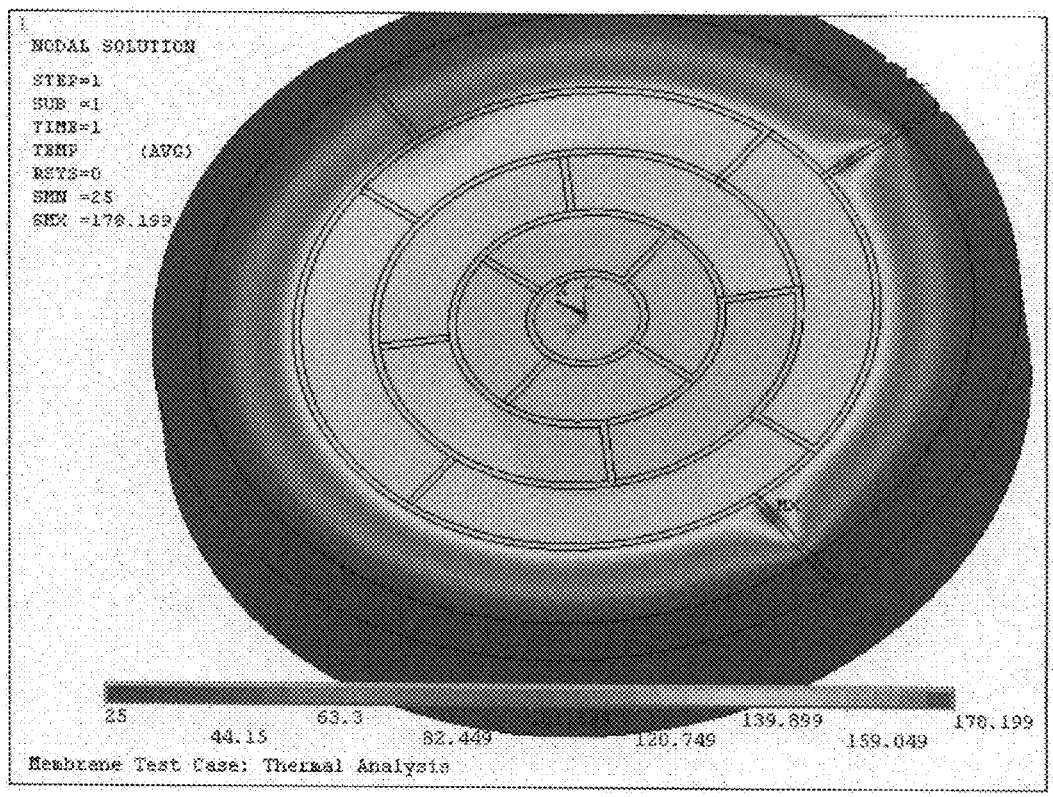
FIG. 13 illustrates ANSYS prediction of the thermal behavior of a 3D preconcentrator with full thickness sorbent zone and reduced thickness thermal isolation support structures is illustrated according to one embodiment of the present invention.

Referring now to FIG. 13, ANSYS prediction of the thermal behavior of a 3D preconcentrator with full thickness sorbent zone and reduced thickness thermal isolation support structures is illustrated according to one embodiment of the present invention. The application of 7.1 V provides 126° C. to a preconcentrator having 25 micron wide walls and 200 micron thick thermal isolation support structures. The thermal isolation support structures are less than full wafer thickness. The substrate has a thickness of greater than 200 um.

Figure 14:
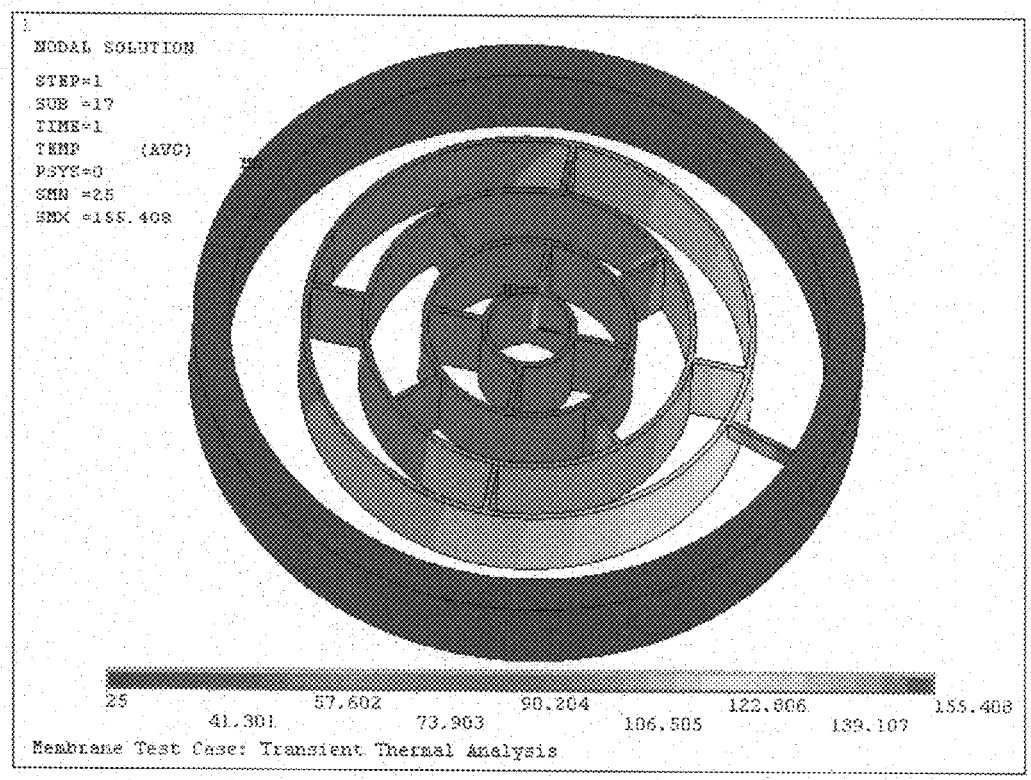
FIG. 14 illustrates ANSYS prediction of the thermal behavior of a 3D preconcentrator with full thickness sorbent zone and reduced thickness thermal isolation support, structures is illustrated according to one embodiment of the present invention.

Referring now to FIG. 14, ANSYS prediction of the thermal behavior of a 3D preconcentrator with full thickness sorbent zone and reduced thickness thermal isolation support structures is illustrated according to one embodiment of the present invention. The SiN layer in this illustration is omitted to show the sorbent zone and thermal isolation support structures suspension however, it is not omitted in the simulation. The illustrated thermal isolation support structure is less than full wafer thickness at about 100 micron thick. 7.1V produces 155° C. The wafer is about 400 rm thick.

Figure 15:
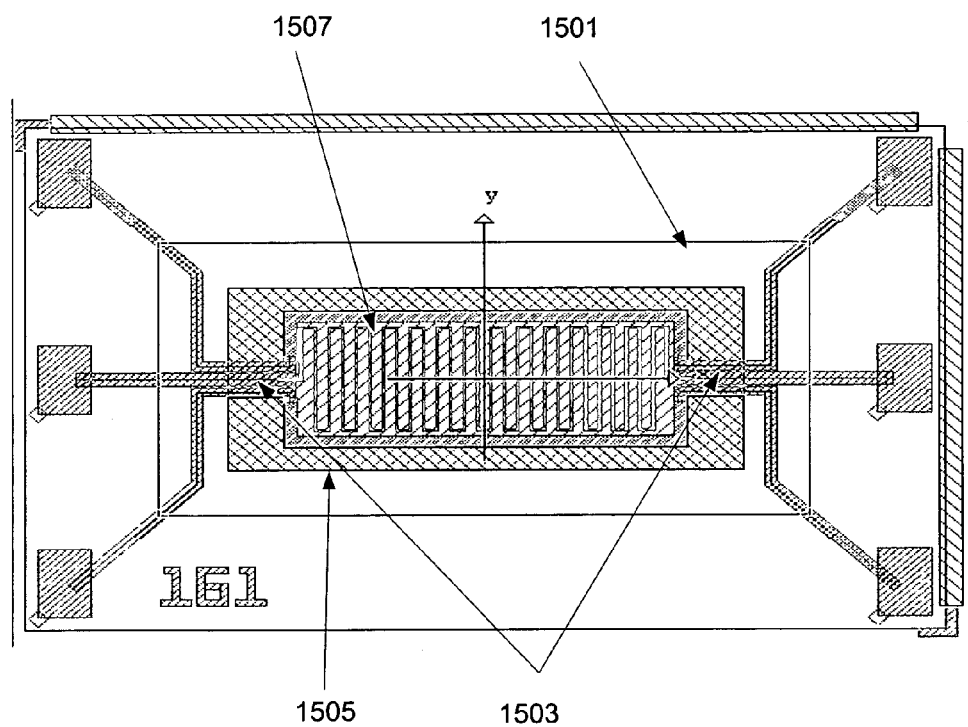
FIG. 15 illustrates a preconcentrator having isolation support structures according to one embodiment of the present invention.

Referring now to FIG. 15, membrane preconcentrator having thermal isolation support structures is illustrated according to one embodiment of the present invention. A heater 1507 is placed on the rectangular active area 1505. The active area 1505 of the device is thermally-isolated from the substrate 1501 by two rectangular thermal isolation support structures 1503 at either side of the active area 1505. The thermal isolation structure may be of any shape. In a preferred embodiment, the thickness of the structure will be less than the full thickness of the substrate. The thermal isolation support structures are about 160 micron wide by 200 micron long. The thickness has been varied in the SOI method of making the structure used here from 2 micron thick to 5 micron thick. For 2 microns, 1750 K/W was achieved.

Figure 16:
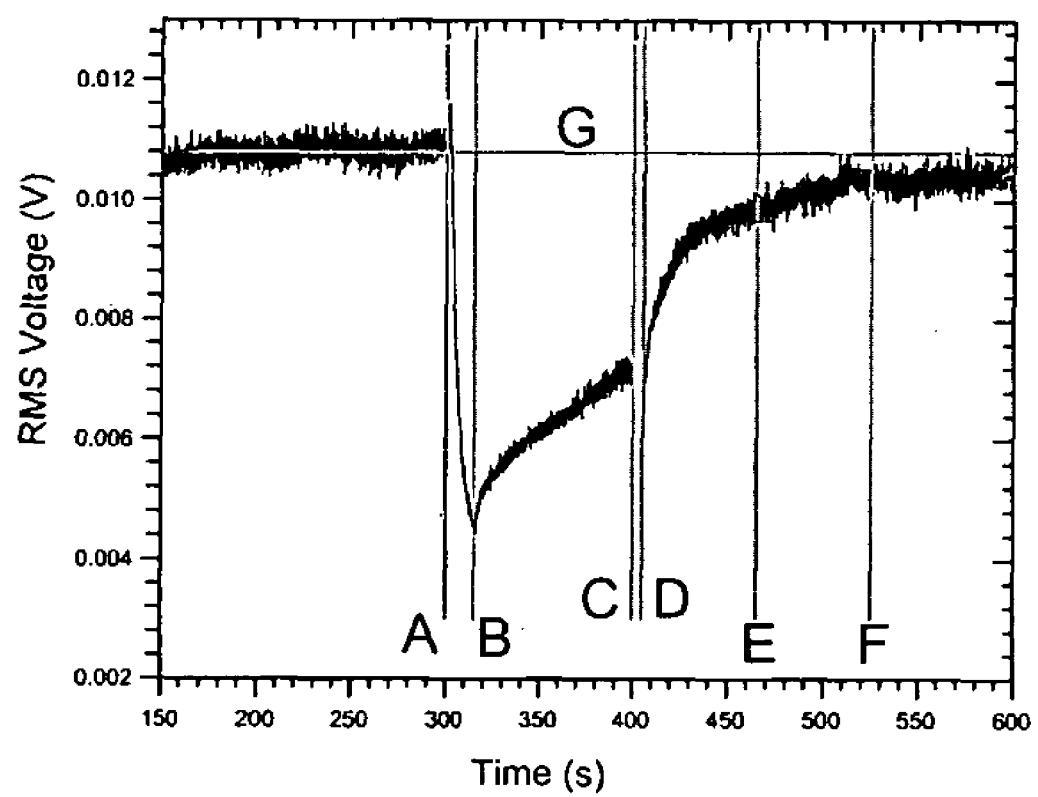
FIG. 16 illustrates collection of DMMP and desorption with preconcentrator having the thermal isolation support structure shown in FIG. 15 according to one embodiment of the present invention.

Referring now to FIG. 16, collection of DMMP and desorption with a preconcentrator according to one embodiment of the present invention as shown in FIG. 15. Point A is a challenge at 300 sec. Point B is an end to the challenge at 315 sec. Point C is release fire at 400 sec with the heater. Point D is end fire at 405 sec. Point E is recovery at 1 minute past end fire. Point F is Recovery at 2 minutes post end fire. Point G is resonant frequency level without the presence of analyte. The time response of the preconcentrator thermally isolated with a thermal isolation support structure is 25 msec to achieve 200° C. from room temperature. The preconcentrator thermally isolated with the thermal isolation support structure has a thermal efficiency of about 1750 K/W on average for an active area of 0.015 cm2. In contrast, the membrane preconcentrator having the following dimensions has a thermal efficiency of about 1200 K/W on average for an active area of 0.032 $cm^2$. By reducing the thermal isolation support structure width from 160 um to less than 160 um, the thermal resistance of the thermal isolation support structure preconcentrator will increase further.

Figure 17:
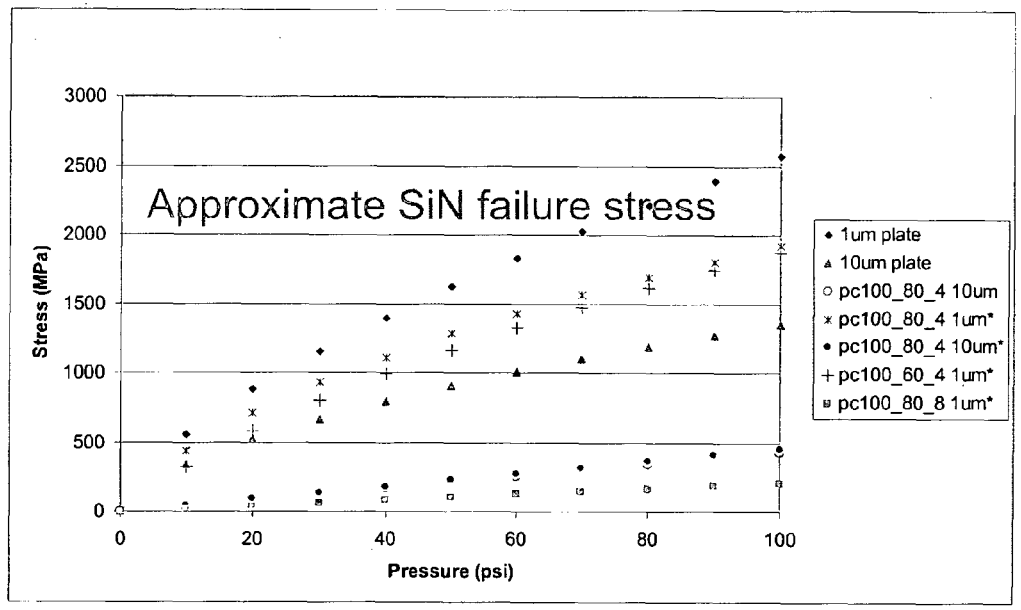
FIG. 17 illustrates a chart of calculated stress at the edge of tortuous path preconcentrators having zero, one or more thermal isolation support structures according to one embodiment of the present invention.

Referring now to FIG. 17, a chart of mechanical stress at the perimeter of a silicon nitride membrane is illustrated as a function of applied pressure. The results for 1 and 10 micron thick membranes is shown. The failure stress of silicon nitride is about 2000 MPa. Adding thermal isolation support structures made of silicon improve the overall strength of the device. The number '100' refers to the separation of tortuous path structures in microns in the active sorbent zone. The numbers '80' or '60' refer to the length in rm of the added silicon thermal isolation supports. '4' and '8' refer to the number of added isolation supports. To prevent analyte from adsorbing on the cold silicon perimeter walls, silicon nitride is utilized. However, the mechanical strength of the device is derived mainly from the silicon thermal isolation support structure and the silicon nitride serves mainly to prevent analyte from approaching cold sidewalls.

A SiN membrane of 1 um thickness (solid diamonds) attached to the wafer reaches failure stress at less than 70 psi. The addition of 4 thermal isolation bridges 200 micron thick (i.e., less than full substrate thickness) and having a length of about 80 um which connects the substrate to the preconcentrator decreases the mechanical stress measure while providing acceptable thermal isolation. At about 2100 MPa SiN membranes fail.

Fabrication methods known in the art are advanced to allow for precise control of the physical dimensions of the preconcentrators thus formed. Precise dimensional control is important for achieving repeatability in operational characteristics of the device, having significant impact on its manufacturability. In each of the various methods for forming the chemical preconcentrator of the present invention, a number of processing steps are required including processes such as material deposition, photolithography, masking, etching, mask stripping and cleaning which are well-known in the semiconductor integrated circuit (IC) industry and MEMS (microelectromechanical system) industry. Therefore only a limited number of processing steps will be described herein.

Figure 18:
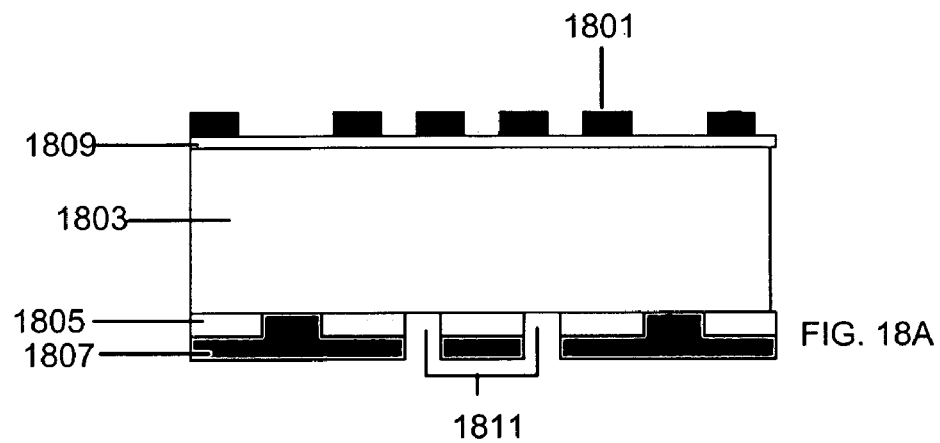
FIG. 18 illustrates a process for manufacture of a preconcentrator according to one embodiment of the present invention.
Figure 18:
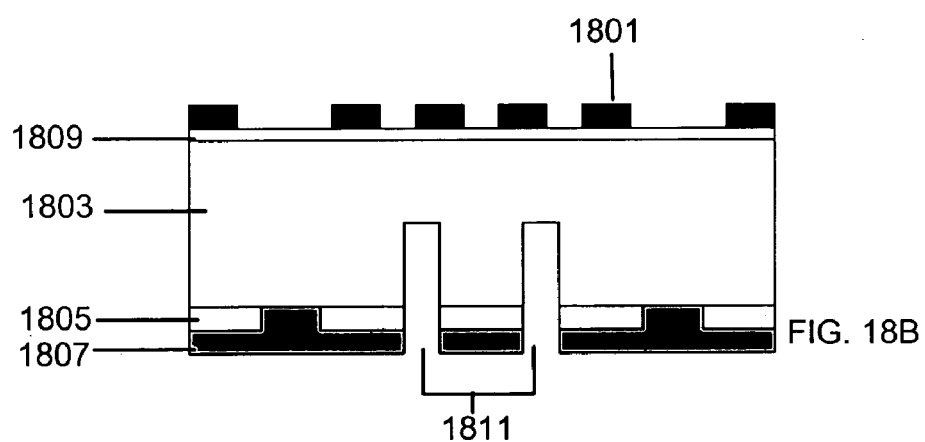
Figure 18:
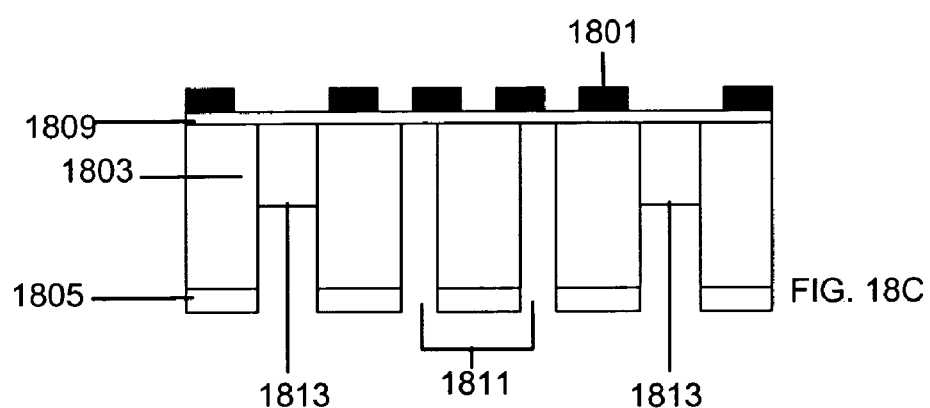

Referring now to FIGS. 18A-C, a cross sectional view of a planar preconcentrator according to one embodiment of the present invention is formed according to one fabrication method. In FIG. 18A, a chip having a suitable substrate 1803 such as silicon with a deposited dielectric 1809 is used as the starting material. A circuitous heater trace 1801 made of metal or semiconductor is patterned on the surface of the dielectric. This will serve ultimately as the resistive heater for the device. The hardmask 1805 is next deposited and patterned on the substrate 1803 such that it is properly aligned to the heater 1801. This can be accomplished through the use of a semiconductor back side mask aligner or other suitable methods known in the art. Typical hardmask materials include hard-baked photoresist, silicon oxide, silicon nitride, metals, etc. The softmask 1807 is then deposited and patterned, aligning either to the hardmask 1805 via typical frontside alignment techniques, or to the metal via techniques aforementioned. The softmask 1807 can be soft-baked photoresist. Openings 1811 in the combined soft mask 1807 and hardmask 1805 layers are used to define features that ultimately progress through the substrate 1803 and stop on the dielectric 1809.

The first etch step shown in FIG. 18B uses the combined mask to etch part way through the substrate 1803, effectively giving regions 1811 a head start over the ultimately-desired thermal isolation structures 1813 of FIG. 18C. For silicon substrates 1803, deep reactive ion etching (DRIE) typical of the Bosch process is used in this step. After this etch step is completed, the softmask 1807 is removed. In the case of a photoresist softmask, this can be accomplished by dipping in acetone or other suitable photoresist strippers. At this point, the partial substrate thickness thermal isolation support structure regions are now open to etching as are the structures already etched in the first etch step. The substrate is then re-inserted into the etch tool such as a DRIE Bosch tool as in FIG. 18C. The structures partially etched through the substrate progress to the dielectric 1809, while the thermal isolation support structures 1813 propagate to a depth set primarily by the difference between the substrate 1803 thickness and the first etch depth. After the second etch step, the hardmask 1805 can be removed in a suitable etchant like acetone.

In another embodiment, a method of making a preconcentrator thermally isolated and supported with one or more thermal isolation support structures captures" a sacrificial layer within the confines of an inert material. The structure of the preconcentrator is formed on top of the sacrificial layer, overlapping the perimeter of the inert layer to provide anchoring. When the sacrificial layer is removed or "released", the physical boundary of the structure is defined by the position of the inert layer. Therefore, the boundary conditions for heat loss are fixed from device to device and are not sensitive to over or under etching of the sacrificial layer. It will be obvious to one of ordinary skill in the art that other methods of forming the thermal isolation support structure preconcentrators are possible, including front-side KOH etching.

A further advantage is the ability to combine the benefits of surface and bulk micromachining to make improved devices. In one embodiment, the active, thermal isolation support structured supported, heating area of the PC is formed in a surface micromachining approach, according to one embodiment of the present invention where a captured sacrificial layer is used. Like the 3D preconcentrator, an sorbent zone structure can then be formed in the thickness of the wafer by bulk micromachining, aligning the support to the surface micromachined heating area using back-side aligning techniques. The sacrificial layer then serves as an etch stop for the bulk micromachining step, greatly improving the repeatability in device fabrication over earlier methods. As a last step, the sacrificial layer is removed. Sacrificial layers and/or other substrates can be used.

As with the 3D preconcentrator, a benefit is the ability to tailor the area of contact between the analyte and the heater and support structures. It was observed that even though the thermal ramp rate of the 3D preconcentrator is orders of magnitude less than the planar device, the desorption peak width is only on the order of a factor of two greater. This implies that the adsorbent support structure is enhancing the collection and release process. The support features can be lithographically defined arbitrarily according to one embodiment of the present invention. Applying surface-and-bulk processing approaches, it is also possible to make direct ohmic contact to the underlying support structure using surface processing techniques. For example, proceeding through the sacrificial layer from the surface thermal isolation support structure to the 3D support, can provide direct electrical contact. Processes typical of the integrated circuit industry would be used to make such contact. The result is direct heating of the support structure, as well as the ability to make diodes in the support structure.

Figure 19:
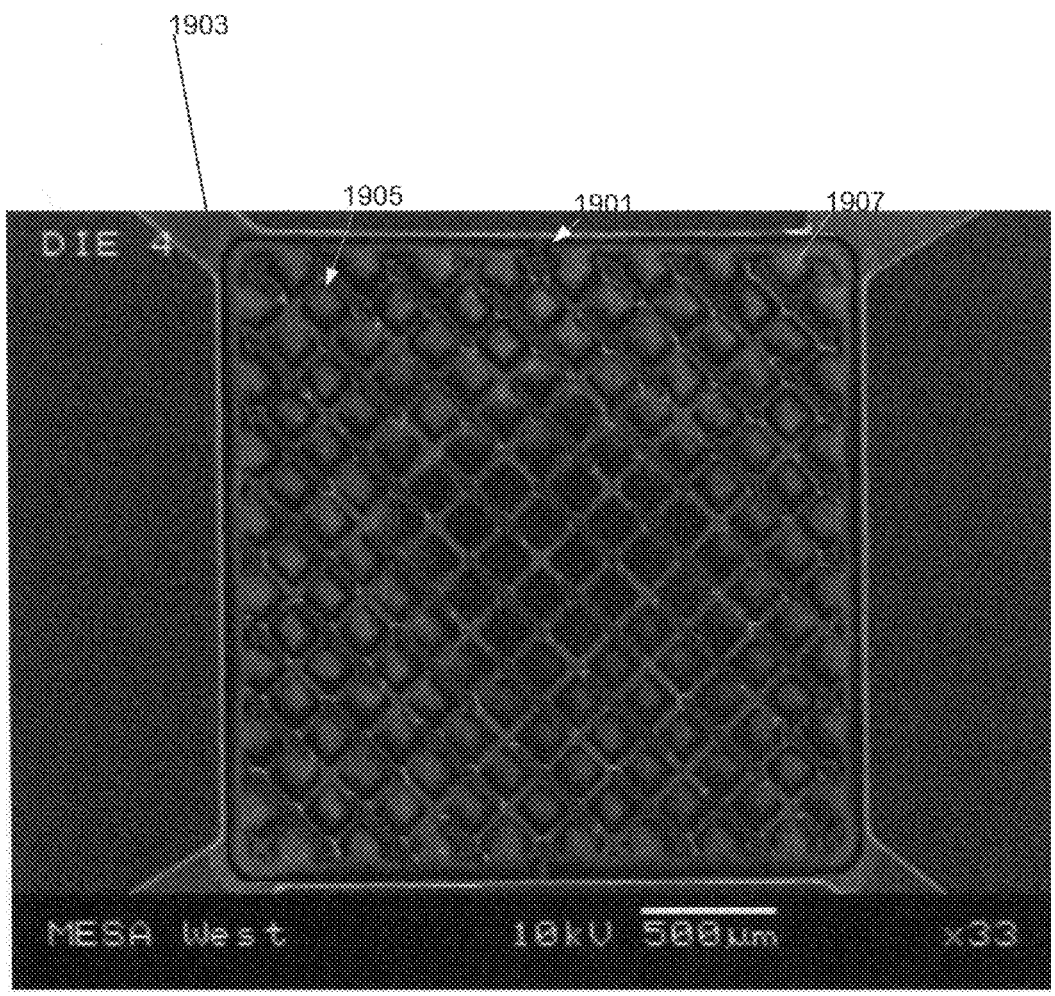
FIG. 19 illustrates one quarter model of a 3 dimensional sorbent zone and heating element according to one embodiment of the present invention.

Referring now to FIG. 19, a sorbent zone and a thermal isolation support structure is illustrated according to one embodiment of the present invention. A thermal isolation support structure 1901 supports the sorbent zone 1905 having a gridlike pattern. A membrane 1907 is suspended from the substrate 1903 and is supported by the sorbent zone 1905.

Figure 20:
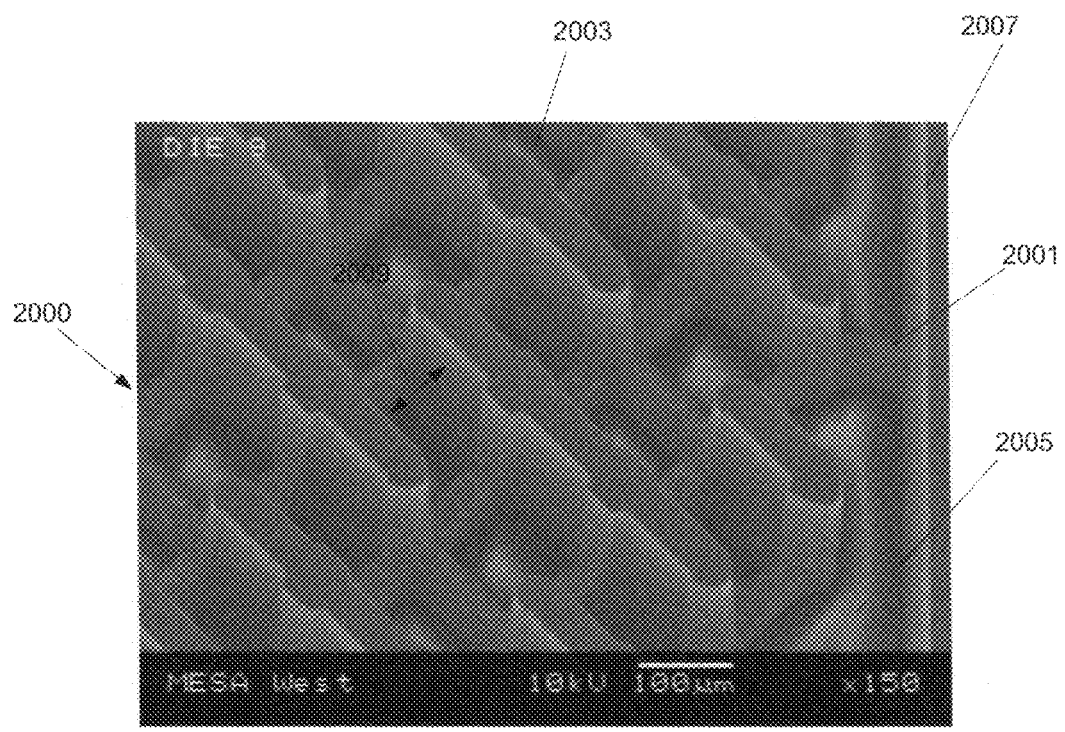
FIG. 20 illustrates an enlarged sorbent zone as shown in FIG. 19.

Referring now to FIG. 20, a portion of FIG. 19 showing a thermal isolation support structure and a sorbent zone 2000 is enlarged. The walls 2003 of the sorbent zone 2000 are fabricated at different depths. The diameter of the pore formed 2009 is about 100 um. A membrane 2005 is supported by the sorbent zone 2000. The sorbent zone 2000 is connected to the substrate 2007 by a thermal isolation support structure 2001. Multi-level silicon based mirostructures can be fabricated by methods known in the art. See U.S. Pat. No. 6,930,051. A heating element associated with microstructures provides heat at a desired rate to a desired temperature to allow chemicals that have been sorbed for example from a gas stream onto a chemically sensitive coating or adsorbent that is disposed on the surface of the multi-level silicon based microstructures.

Compared with the membrane supported planar preconcentrator, embodiments of the present invention allow for easier integration with other microanalytical components like detectors and GC columns. The ease of integration results from the ability to make flow-through adsorbent supports in the surface or in the bulk that are fluidically coupled to other microanalytical components monolithically. As with the 3D preconcentrator, the preconcentrator thermally isolated and supported by the thermal isolation support structure design is pressure balanced, since the structure is immersed in the fluid it is interacting with, whereas with the planar membrane design, pressure fluctuations could rupture the membrane.

The present invention has been described in terms of preferred embodiments, however, it will be appreciated that various modifications and improvements may be made to the described embodiments without departing from the scope of the invention. The entire disclosure of all references, applications, patents and publications cited above and or in the attachments, and of the corresponding application(s) are hereby incorporated by reference.

What is claimed is:

1. A chemical preconcentrator apparatus comprising:
    a resistive heating element disposed on a first portion of a substrate;
    a sorptive material to sorb and concentrate at least one chemical species of interest from a vapor over time, said at least one chemical species being releasable from said sorptive material upon heating of said sorptive material by said heating element, said sorptive material disposed on said heating element to create a sorbent zone; and
    a plurality of thermal isolation support structures fabricated from a second portion of said substrate that connects said first portion of said substrate to a third portion of said substrate, with each thermal isolation support structure fabricated from said second portion of said substrate having a thickness that is less than a thickness of the third portion of said substrate and with a width that is less than a width of the first portion of said substrate.

2. The apparatus of claim 1 wherein said first portion of said substrate has a thickness that is the same or less than the third portion of said substrate.

3. The apparatus of claim 1 wherein a thickness of each thermal isolation support structure is between about 90% and 0.5% of said thickness of said third portion of said substrate.

4. The apparatus of claim 3 wherein each thermal isolation support structure has a thickness that is between about 75% and about 90% of said thickness of said third portion of said substrate.

5. The apparatus of claim 1 wherein the sorptive material comprises a microporous material.

6. The apparatus of claim 1 wherein the sorptive material comprises a chromatographic stationary phase, getter, sol-gel or polymer.

7. The apparatus of claim 6 wherein the sorptive material comprises a sol-gel oxide.

8. The apparatus of claim 7 wherein the sol-gel oxide is chemically modified to enhance sorption of the chemical species of interest.

9. The apparatus of claim 7 wherein the sorptive material comprises a polymer.

10. The apparatus of claim 1 wherein the substrate is selected from the group consisting of semiconductors and dielectrics.

11. The substrate of claim 1 wherein the substrate comprises silicon.

12. The apparatus of claim 1 wherein the resistive heating element comprises a circuitous metal trace.

13. A method for forming a preconcentrator apparatus comprising:
    forming a resistive heating element on a first portion of a substrate;
    disposing a sorptive material capable of sorbing chemical species of interest onto a surface of said resistive heating element to form a sorbent zone;
    reducing the thickness and width of a second portion of said substrate to form a plurality of thermal isolation support structures that connect said first portion of said substrate with a third portion of said substrate, said third portion of said substrate having a thickness that is greater than the thickness of each thermal isolation support structure and said first portion having a width that is greater than the width of each thermal isolation support structure.

14. The method of claim 13 wherein a thickness of each thermal isolation support structure is between about 90% and 0.5% of said thickness of said third portion of said substrate.

15. The method of claim 14 wherein each thermal isolation support structure has a thickness that is between about 75% and about 90% of said thickness of said third portion of said substrate.

16. The method of claim 13 wherein the sorptive material comprises a microporous material.

17. The method of claim 13 wherein the sorptive material comprises a chromatographic stationary phase, getter, sol-gel or polymer.

18. The method of claim 13 wherein the sorptive material comprises a sol-gel oxide.

19. The method of claim 18 wherein the sol-gel oxide is chemically modified to enhance sorption of the chemical species of interest.

20. The method of claim 19 wherein the sorptive material comprises a polymer.

21. The method of claim 13 wherein the substrate is selected from the group consisting of semiconductors and dielectrics.

22. The method of claim 13 wherein the substrate comprises silicon.

23. The method of claim 13 wherein the resistive heating element comprises a circuitous metal trace.

24. The apparatus of claim 1 wherein the plurality of thermal isolation support structures comprises two thermal isolation support structures located on opposite sides of the sorbent zone.

25. The apparatus of claim 1 wherein the sorbent zone has a gridlike pattern with a plurality of walls with different depths.

26. The apparatus of claim 25 further comprising a membrane supported by the sorbent zone.

27. A chemical preconcentrator apparatus comprising a substrate having a sorbent zone suspended from the substrate by a plurality of thermal isolation support structures, with the sorbent zone comprising a resistive heating element and a sorptive material to sorb and concentrate at least one chemical species of interest from a vapor over time, and with the chemical species being releasable from the sorbent zone upon heating of the sorptive material by the resistive heating element, and with each thermal isolation support structure having a thickness which is smaller than the thickness of the substrate and with all lateral dimensions of each thermal isolation support structure being smaller than the lateral dimensions of the sorbent zone.

* * * * *